US012667641B2

(12) United States Patent
Jobeili et al.

(10) Patent No.: US 12,667,641 B2
(45) Date of Patent: Jun. 30, 2026

(54) BIOMATERIAL COMPRISING A RESORBABLE POROUS MATRIX AND ASSOCIATED MANUFACTURING METHOD

(71) Applicants: UNIVERSITE GRENOBLE ALPES, Saint Martin D'Heres (FR); COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

(72) Inventors: Lara Marwa Jobeili, Grenoble (FR); Alexandre Gaston Mickaël Lellouch, Levallois-Perret (FR); Walid Rachidi, Meylan (FR); Laurent Alexandre Lantieri, Paris (FR)

(73) Assignees: UNIVERSITE GRENOBLE ALPES, Saint Martin D'Heres (FR); COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 765 days.

(21) Appl. No.: 17/915,676

(22) PCT Filed: Mar. 29, 2021

(86) PCT No.: PCT/EP2021/058151
§ 371 (c)(1),
(2) Date: Sep. 29, 2022

(87) PCT Pub. No.: WO2021/198177
PCT Pub. Date: Oct. 7, 2021

(65) Prior Publication Data
US 2023/0120975 A1     Apr. 20, 2023

(30) Foreign Application Priority Data
Mar. 30, 2020    (FR) ...................................... 2003125

(51) Int. Cl.
| | |
|---|---|
| *A61L 24/00* | (2006.01) |
| *A61K 35/33* | (2015.01) |
| *A61L 24/10* | (2006.01) |
| *A61L 27/38* | (2006.01) |
| *A61P 17/02* | (2006.01) |

(52) U.S. Cl.
CPC .......... *A61L 24/0036* (2013.01); *A61K 35/33* (2013.01); *A61L 24/102* (2013.01); *A61L 27/3886* (2013.01); *A61P 17/02* (2018.01)

(58) Field of Classification Search
CPC ............... A61L 24/0036; A61L 24/102; A61L 27/3886; A61P 17/02; A61K 35/33
See application file for complete search history.

(56) References Cited

U.S. PATENT DOCUMENTS

| | | | |
|---|---|---|---|
| 5,166,187 | A | 11/1992 | Collombel et al. |
| 5,282,859 | A | 2/1994 | Eisenberg |
| 5,945,101 | A | 8/1999 | Berg et al. |
| 6,153,292 | A | 11/2000 | Bell et al. |
| 2006/0135921 | A1 | 6/2006 | Wiercinski et al. |
| 2008/0281431 | A1* | 11/2008 | Missos ................. A61L 27/427 |
| | | | 623/23.6 |

FOREIGN PATENT DOCUMENTS

| | | |
|---|---|---|
| FR | 2809313 A1 | 11/2001 |
| WO | 8810123 A1 | 12/1988 |

OTHER PUBLICATIONS

Vaissiere et al., "Comparative analysis of different collagen-based biomaterials as scaffolds for long-term culture of human fibroblasts", Medical and Biological Engineering and Computing, 2000, vol. 38, No. 2, p. 205-210.
Ramsey et al., "Full thickness skin grafts", StatPearls. StatPearls Publishing, Treasure Island (FL), 2022.
Shimizu et al., "Skin graft", Plastic surgery international, 2012, vol. 2012.
International Search Report and Written Opinion issued in corresponding International Application No. PCT/EP2021/058151, mailed May 28, 2021, pp. 1-9, European Patent Office, Rijswijk, Netherlands.
"Living tissue formed in vitro and accepted as skin-equivalent tissue of full thickness", Bell et al., Science, 1981, vol. 211, No. 4486, p. 1052-1054.
"Review of the current management of pressure ulcers", Boyko et al., Advances in wound care, 2018.
"Current wound healing procedures and potential care", Dreifke et al., Materials Science and Engineering: C, 2015, vol. 48, p. 651-662.
"Epidermal differentiation governs engineered skin biomechanics", Ebersole et al., Journal of biomechanics, 2010, vol. 43, No. 16, p. 3183-3190.
"Apligraf in the treatment of neuropathic diabetic foot ulcers", Edmonds et al., The international journal of lower extremity wounds, 2009, vol. 8, No. 1, p. 11-18.
"Chronic wound healing: a review of current management and treatments", Han et al., Advances in therapy, 2017, vol. 34, No. 3, p. 599-610.

(Continued)

*Primary Examiner* — Shirley V Gembeh
(74) *Attorney, Agent, or Firm* — HAUPTMAN HAM, LLP

(57) ABSTRACT

A biomaterial including a resorbable porous matrix formed from a material including collagen, and exhibiting an inner volume and an outer surface. Advantageously, the biomaterial includes at least one type of living biological cells of a tissue, disposed in the inner volume and alternatively or complementarily on the surface of the porous matrix. The biomaterial forms a tissue substitute being close to a native tissue, in particular in terms of biological structure present in the tissue, and physiological functions.

17 Claims, 6 Drawing Sheets

(56)                    References Cited

OTHER PUBLICATIONS

"Prevalence and incidence of chronic wounds and related complications: a protocol for a systematic review", Järbrink et al., Systematic reviews, 2016, vol. 5, No. 1, p. 1-6.

"A new type of biomaterial for artificial skin: Dehydrothermally cross-linked composites of fibrillar and denatured collagens", Koide et al., Journal of biomedical materials research, 1993, vol. 27, No. 1, p. 79-87.

"Diabetic neuropathic foot ulcers: the association of wound size, wound duration, and wound grade on healing", Margolis et al., Diabetes care, 2002, vol. 25, No. 10, p. 1835-1839.

"Prevalence of chronic wounds in the general population: systematic review and meta-analysis of observational studies", Martinengo et al., Annals of epidemiology, 2019, vol. 29, p. 8-15.

NHS. Treatment of Pressure Ulcers. National Health Service UK (2015). Available at: https://www.nhs.uk/conditions/pressure-sores/treatment/.

"IDF Diabetes Atlas: Global estimates for the prevalence of diabetes for 2015 and 2040", Ogurtsova et al., Diabetes research and clinical practice, 2017, vol. 128, p. 40-50.

"Classification of Burns", Perez et al., University of Rochester Medical Center (2018). Available at: https://www.urmc.rochester.edu/encyclopedia/content.aspx?ContentTypeID=90&ContentID=P09575.

"Guidelines for the treatment of venous ulcers", Robson et al., Wound repair and regeneration: official publication of the Wound Healing Society [and] the European Tissue Repair Society, 2006, vol. 14, No. 6, p. 649-662.

"Percent change in wound area of diabetic foot ulcers over a 4-week period is a robust predictor of complete healing in a 12-week prospective trial", Sheehan et al., Diabetes care, 2003, vol. 26, No. 6, p. 1879-1882.

"An instrument to measure healing in pressure ulcers: development and validation of the pressure ulcer scale for healing (PUSH)", Stotts et al. The Journals of Gerontology Series A: Biological Sciences and Medical Sciences, 2001, vol. 56, No. 12, p. M795-M799.

"Cellular versus acellular matrix devices in the treatment of diabetic foot ulcers: Interim results of a comparative efficacy randomized controlled trial", Tchanque-Fossuo et al., Journal of tissue engineering and regenerative medicine, 2019, vol. 13, No. 8, p. 1430-1437.

"Fibroblast behavior on gels of type I, III, and IV human placental collagens", Tiollier et al., Experimental cell research, 1990, vol. 191, No. 1, p. 95-104.

"Randomized, prospective, blinded-enrollment, head-to-head venous leg ulcer healing trial comparing living, bioengineered skin graft substitute (Apligraf) with living, cryopreserved, human skin allograft (TheraSkin)", Towler et al., Clinics in podiatric medicine and surgery, 2018, vol. 35, No. 3, p. 357-365.

"Venous leg ulcers: pathophysiology and classification", Vasudevan, Biju, Indian dermatology online journal, 2014, vol. 5, No. 3, p. 366.

"Advances in skin regeneration using tissue engineering", Vig et al., International journal of molecular sciences, 2017, vol. 18, No. 4, p. 789.

"Diagnosis and treatment of venous leg ulcers", Werchek et al., The Nurse Practitioner, 2010, vol. 35, No. 12, p. 46-53.

"Design of an artificial skin. I. Basic design principles", Yannas et al., Journal of biomedical materials research, 1980, vol. 14, No. 1, p. 65-81.

"Literature review on the management of diabetic foot ulcer", Yazdanpanah et al., World journal of diabetes, 2015, vol. 6, No. 1, p. 37.

"Treatment of chronic diabetic lower extremity ulcers with advanced therapies: a prospective, randomised, controlled, multi-centre comparative study examining clinical efficacy and cost", Zelen et al., International wound journal, 2016, vol. 13, No. 2, p. 272-282.

"Global epidemiology of diabetic foot ulceration: a systematic review and meta-analysis", Zhang et al., Annals of medicine, 2017, vol. 49, No. 2, p. 106-116.

* cited by examiner

3

11,111,1110

1010

11,110,1100

1011

10

101

100

1012

1

112,1120
11'
1111
112,1121
11'

11,111,1110'

1010

10+
11,110,1100

1

11'

11'
112,1122
112,1123

11,111,1110'

1010

10+
11,110,1100

BIOMATERIAL COMPRISING A RESORBABLE POROUS MATRIX AND ASSOCIATED MANUFACTURING METHOD

The present application is a U.S. National Phase of International Application Number PCT/EP2021/058151, filed Mar. 29, 2021, which claims priority to French Application No. 2003125, filed Mar. 30, 2020, the entirety of which is incorporated herein by referein.

TECHNICAL FIELD

The present invention relates to the field of biomaterials comprising collagen and their manufacturing. It has a particularly advantageous application in the field of dermoepidermal substitutes.

STATE OF THE ART

Chronic wounds represent a major public health problem affecting more than 2 million people, only in mainland France. This includes physical burns, for example induced by ultraviolet radiation, and chemical burns, for example induced by detergents or acids, ulcers, and in particular pressure ulcers, venous ulcers and diabetic ulcers. These chronic wounds generally require the replacement of injured tissues, for example by a skin graft.

For the particular case of skin grafts, there are different types of grafts, classified according to the thickness of skin removed on the person:

the graft of thin skin is removed by an electric dermatome with a thickness of 0.2 to 0.3 mm on a donor area of the body of the patient, generally an internal face of the thigh or of the scalp. This removal is then transferred to a recipient area (using stitching or stapling) of the patient for an autologous graft. This technique can be completed with the addition of an artificial dermal substitute such as Integra®. The main disadvantage resides in sequelae induced by the removal and the limited surface of the donor areas;

the total skin graft, does not require removal with the dermatome like for a thin skin graft. A fusiform incision is performed in a skin fold, for example the supraclavicular fold. The skin is then defatted (to enable a better gripping of the graft), then sutured on the recipient area. This technique is considered as particularly suitable for the face.

The removals of skin tissues in the scope of grafts however remain limited, in particular in terms of available surface of donor areas and pains induced in the person having the removal.

Moreover, since 2013, dermocosmetic product effectiveness and safety tests are prohibited on animals. To test these substances, the pharmaceutical or cosmetics industry must therefore resort to tissue substitutes mimicking, at best, the properties and the reactions of a native tissue.

There is therefore a need to develop a tissue substitute closest to a native tissue, for example for the treatment of chronic wounds or for pharmacological or cosmetic applications.

A biomaterial comprising a compound constituted of collagen, acetyl chitosan and glycosaminoglycans is known, from document WO 88/10123 A1. This biomaterial can constitute the dermal layer of an artificial skin, and be associated with a biodegradable pseudo epidermis, for example a chitosan film. However, this biomaterial remains improvable to mimic a native skin.

An aim of the present invention is therefore to propose a biomaterial moving closer to a native tissue.

The other aims, features and advantages of the present invention will appear, upon examining the following description and accompanying drawings. It is understood that other advantages can be incorporated.

SUMMARY

To achieve this aim, according to a first aspect, a biomaterial is provided, comprising a resorbable porous matrix formed from a material comprising collagen, and exhibiting an inner volume and an outer surface.

Advantageously, the biomaterial comprises at least one type of living biological cells of a tissue, disposed in the inner volume and, alternatively or complementarily, on the surface of the porous matrix.

Thus, the biomaterial comprises a matrix giving it a structure enabling its manipulation, and biological cells of a tissue seeded in the porous matrix. The biomaterial therefore forms a tissue substitute close to a native tissue, in particular in terms of biological structure present in the tissue, and of physiological functions.

Furthermore, with the matrix being resorbable, the porous matrix can be degraded to facilitate the integration of a part of the biomaterial in the organism, and more specifically, of a tissue formed by the biological cells, for example following a graft of the biomaterial. The biomaterial therefore forms a tissue substitute which could be grafted on an organism, then act directly to perform its tissue function, without further requiring the removal of the biomaterial, and more specifically of the porous matrix.

According to an example, the at least one type of living biological cells of a tissue are disposed in the inner volume of the porous matrix.

A second aspect of the invention relates to a method for manufacturing a biomaterial comprising:

a supply of a resorbable porous matrix formed from a material comprising collagen, then a seeding of the porous matrix by at least one type of living biological cells of a tissue, then a cell growth of the at least one type of biological cells.

The method thus makes it possible to obtain the biomaterial according to the first aspect of the invention. By seeding and growth, a biomaterial of size and form, variable according to the dimensions of the porous matrix can further be formed. Thus, a biomaterial forming a tissue substitute close to a native tissue is obtained.

A third aspect relates to the use of a biomaterial, the biomaterial comprising:

a resorbable porous matrix formed from a material comprising collagen, and exhibiting an inner volume and a surface, and at least one type of living biological cells of a tissue, disposed in the inner volume and, alternatively or complementarily, on the surface of the porous matrix, for an in vitro application of at least one substance chosen from among a pharmaceutical substance and a cosmetic substance.

A fourth aspect relates to the use of a biomaterial for the treatment of lesions, and more specifically the treatment of skin lesions, the biomaterial comprising:

a resorbable porous matrix formed from a material comprising collagen, and exhibiting an inner volume and a surface, and at least one type of living biological cells of a tissue, in the inner volume and, alternatively or complementarily, on the surface of the porous matrix.

A fifth aspect relates to a biomaterial intended to be grafted on an organism, for example for the treatment of a lesion, and more specifically, the treatment of skin lesions, the biomaterial comprising:

a resorbable porous matrix formed from a material comprising collagen, and exhibiting an inner volume and a surface, and at least one type of living biological cells of a tissue, disposed in the inner volume and, alternatively or complementarily, on the surface of the porous matrix.

A combinable or separable aspect relates to a dermoepidermal substitute comprising a resorbable porous matrix formed from a material comprising collagen, and exhibiting an inner volume and an outer surface, the dermoepidermal substitute being characterised in that it comprises living skin cells, disposed in the inner volume of the porous matrix, an extracellular matrix disposed in the inner volume, the extracellular matrix being secreted by the skin cells, and epidermal cells disposed on the outer surface of the porous matrix.

BRIEF DESCRIPTION OF THE FIGURES

The aims, objectives, as well as the features and advantages of the invention will emerge best from the detailed description of an embodiment of the latter, which is illustrated by the following accompanying drawings, wherein.

Figure 1:
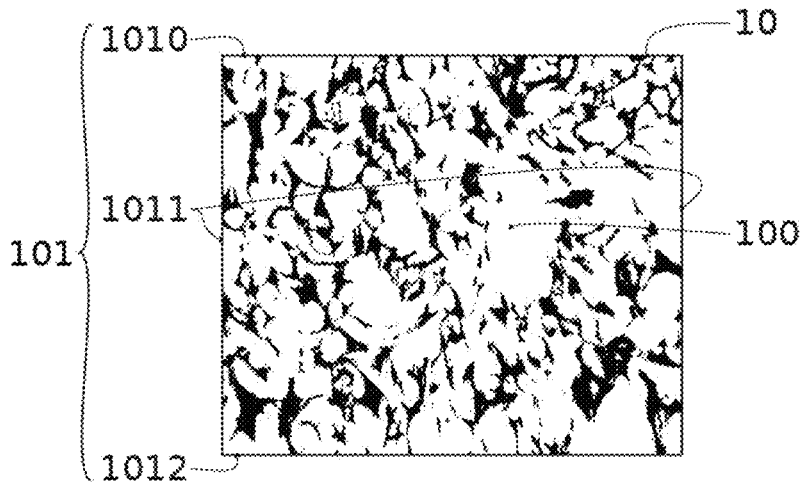
FIG. 1 represents a transverse cross-sectional view of the porous matrix according to an embodiment of the invention.

The drawings are given as examples and are not limiting of the invention. They constitute schematic representations of principle, intended to facilitate the understanding of the invention and are not necessarily to the scale of practical applications. In particular, the relative dimensions of the biological cells between them and relative to the porous matrix are not representative of reality.

DETAILED DESCRIPTION

Before starting a detailed review of embodiments of the invention, optional features are stated below, which can optionally be used in association or alternatively for each of the aspect of the invention:

the at least one first type of biological cells can be disposed at least in the inner volume of the porous matrix, even only in the inner volume of the matrix, the at least one first type of biological cells can be disposed at least on an outer surface of the porous matrix, even only on a surface of the matrix, and preferably on an upper face of the porous matrix, the porous matrix can be biocompatible, the material of the porous matrix can comprise at least 90%, preferably at least 95%, and more specifically, at least 99% by mass of collagen, relative to the dry mass of the porous matrix, the material of the porous matrix can have no chitosan, the porous matrix can be chosen from among a gel, a powder, and a sponge. Preferably, the porous matrix is chosen from among a powder and a sponge, the porous matrix can be a synthetic sponge, and more specifically, a haemostatic sponge. Thus, the porous matrix can be available commercially and at a reduced cost, the porous matrix can be a product serving Good Manufacturing Practices (GMP). The porous matrix can be clinically usable in humans or animals. The biomaterial can thus be clinically usable in humans or animals, the biological cells can comprise cells chosen from among conjunctive tissue cells, epithelial and endothelial cells. According to an example, the conjunctive tissue cells are so-called fibroblastic skin cells and/or subcutaneous fat tissue cells called stem cells of the fat tissue. According to an example, the epithelial cells are skin cells comprising keratinocytes and/or melanocytes. According to an example, the endothelial cells are vessel cells. Preferably, the biological cells are human or animal cells, the at least one type of biological cells can be disposed at least in the inner volume of the porous matrix, even only in the inner volume of the matrix, the biomaterial can further comprise an extracellular matrix at least in said inner volume, the extracellular matrix being secreted by the at least one first type of biological cells. The biological cells and their extracellular matrix make it possible to form a tissue in the porous matrix, and are closer to the properties of a native tissue, a first type of biological cells can be disposed in the inner volume of the porous matrix, and the biomaterial can comprise at least one second type of biological cells disposed on the surface, for example, the upper face, of the porous matrix, the second type of biological cells could further be distinct from the first type of biological cells. Thus, the biomaterial can further comprise a cell layer on the surface of the porous matrix forming an external limit of a tissue, and is closer to a native tissue. According to an example, the second type of biological cells is a type of epithelial cells. Thus, the biomaterial exhibits barrier properties. The biomaterial therefore enables the replacement of the barrier function, for example on a wound not healing spontaneously, such as a chronic wound, the first type of biological cells can comprise skin cells, for example, fibroblastic, and the second type of biological cells can comprise epithelial cells, for example keratinocytes, even further melanocytes. According to an example, the first type of biological cells can further comprise at least one type of biological cells from among endothelial cells, immune cells, stem cells or fat tissue. According to an example, the at least one second type of biological cells can further comprise melanocytes, the biological cells are chosen from among cells derived from standard cell line cultures, and preferably isolated primary cells of a biological sample of an organism. According to an example, the biomaterial can comprise autologous or allogenic cells. According to an example, the biological cells are isolated from a skin sample of a person.

Optional features of the second aspect of the invention are stated below, which can optionally be used in association or alternatively:

the method can comprise a hydration of the porous matrix so as to balance the pH and the osmolarity of the porous matrix, prior to the seeding. According to an example, the hydration is performed with at least one buffered solution, then with a culture medium, the hydration of the porous matrix can be performed by a hydration solution exhibiting a pH of between 6.8 and 7.5, and/or an osmolarity of between 270 and 360 mmol/kg, the method can further comprise a drying of the porous matrix between the hydration of the porous matrix and the seeding of the porous matrix. According to an example, the drying of the porous matrix is performed by aspiration, for example of the hydration solution, the seeding of the porous matrix can be performed by deposition of a suspension of the at least one type of biological cells on the porous matrix. According to an example, the at least one type of biological cells can be seeded at a cell density of between $0.5.10^6$ cells/cm$^2$ and $1.10^6$ cells/cm$^2$, the cm$^2$ being given with reference to the surface of the porous matrix, the method can further comprise, after a first seeding by a first type of biological cells, even after the first seeding and at least some of a cell growth of the first type of biological cells, a second seeding of the porous matrix by at least one second type of biological cells, distinct from a first type of seeded biological cells. The method can then further comprise a cell growth of the at least one second type of biological cells, the method can further comprise a drying of the porous matrix prior to the second seeding of the porous matrix, the drying, preferably, each drying, of the porous matrix can comprise an aspiration of the solution or of the medium present in the porous matrix, and the placement of the porous matrix on an absorbent support, preferably, the porous matrix is placed on the absorbent support after the aspiration, the absorbent support can comprise a sterile compress, the absorbent support can comprise a sterile blotting paper, the sterile compress is preferably deposited on a sterile blotting paper, the second seeding can be performed by deposition of a suspension of at least one second type of biological cells on the porous matrix, the biological cells can comprise conjunctive cells chosen from among conjunctive tissue cells and epithelial cells, when the biological cells are conjunctive tissue cells, the cell growth can comprise an immersion of the porous matrix in a culture medium. Preferably, the porous matrix is fully immersed. Furthermore, the porous matrix can be immersed for the majority of the cell growth, when the biological cells are epithelial cells, the cell growth can comprise a first undergrowth, during which the porous cell is immersed in a culture medium, until a confluence of the biological cells on the surface of the porous matrix, the cell growth can comprise, following the first undergrowth, a second undergrowth, could equally be designated at maturing, during which the porous matrix is placed at an interface between air and a culture medium. The maturing makes it possible to differentiate epithelial cells to form a more complex, even complete epidermis, and is close to a native tissue.

It is specified that in the scope of the present invention, the term "resorbable matrix" means the fact that the matrix is biodegradable from the cells, for example from an organism.

By a "biocompatible" matrix, this means that the matrix is configured to not interfere, even not degrade, a biological medium in contact with which the matrix is disposed. More specifically, the matrix is tolerated by an organism in or on which the matrix is in contact, for example by grafting. More specifically, the organism exhibits a low level of inflammatory reaction, even, an absence of inflammatory reaction induced by the contact of the matrix, for example, by grafting.

By a parameter "substantially equal to/greater than/less than" a given value, this means that this parameter is equal to/greater than/less than a given value, roughly 10%, even roughly 5%, of this value.

By porosity of the matrix, this means the proportion of vacuum or gas in the matrix.

Below in the description, use will be made of terms such as "transverse", "upper" and "lower". These terms must be interpreted relatively, relative to the normal position of use of the biomaterial. For example, in the case, the porous matrix is intended to be deposited on a support, the lower face corresponds to the face intended to be rotated to the support. According to this example, the upper face corresponds to the face intended to be rotated opposite the support.

Figure 5A:
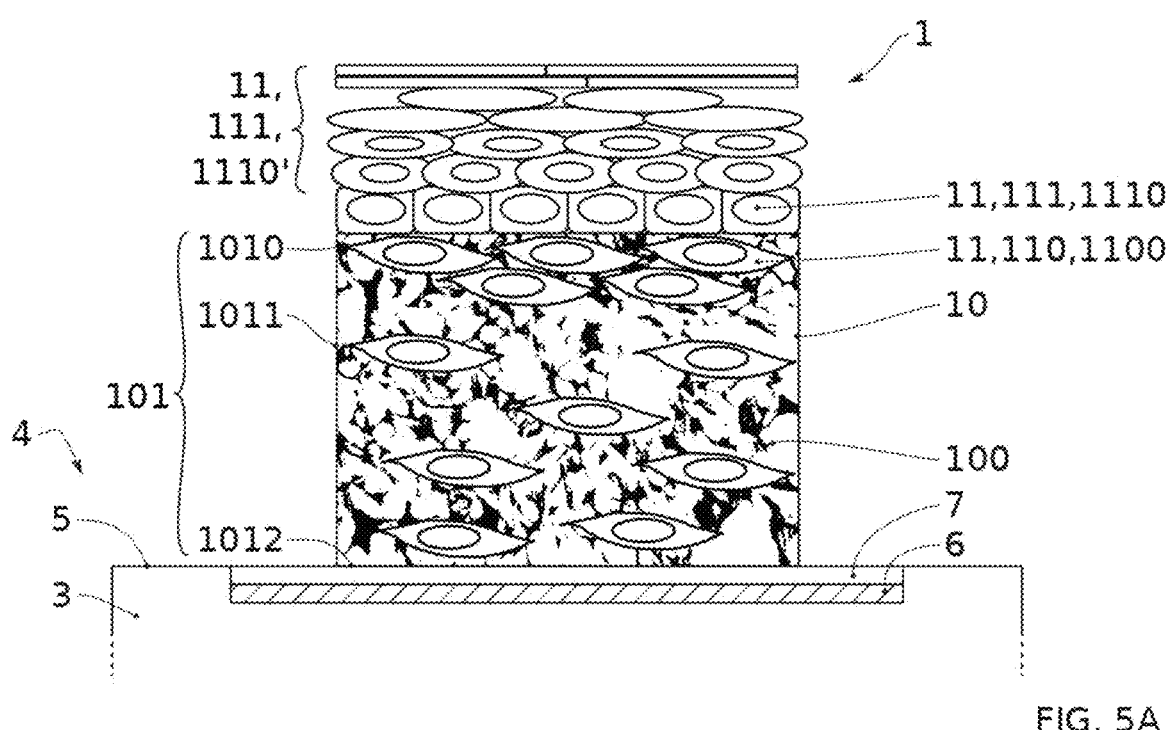
FIG. 5A represents a maturing of the second type of biological cells following the first cell undergrowth illustrated in FIG. 4, according to an embodiment of the invention.
Figure 5B:
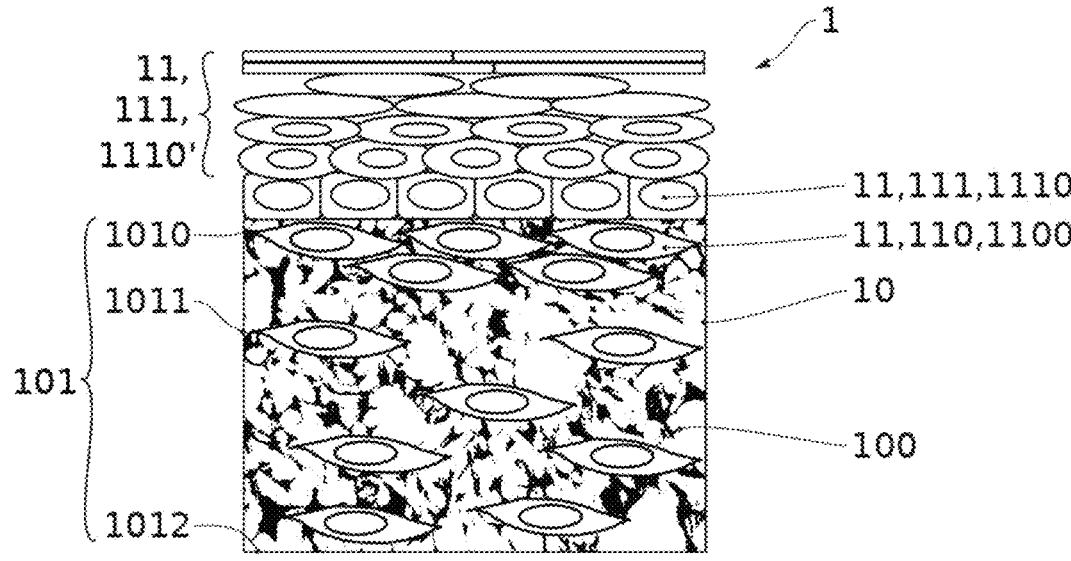
FIG. 5B represents the biomaterial, according to an embodiment of the invention.
Figure 6:
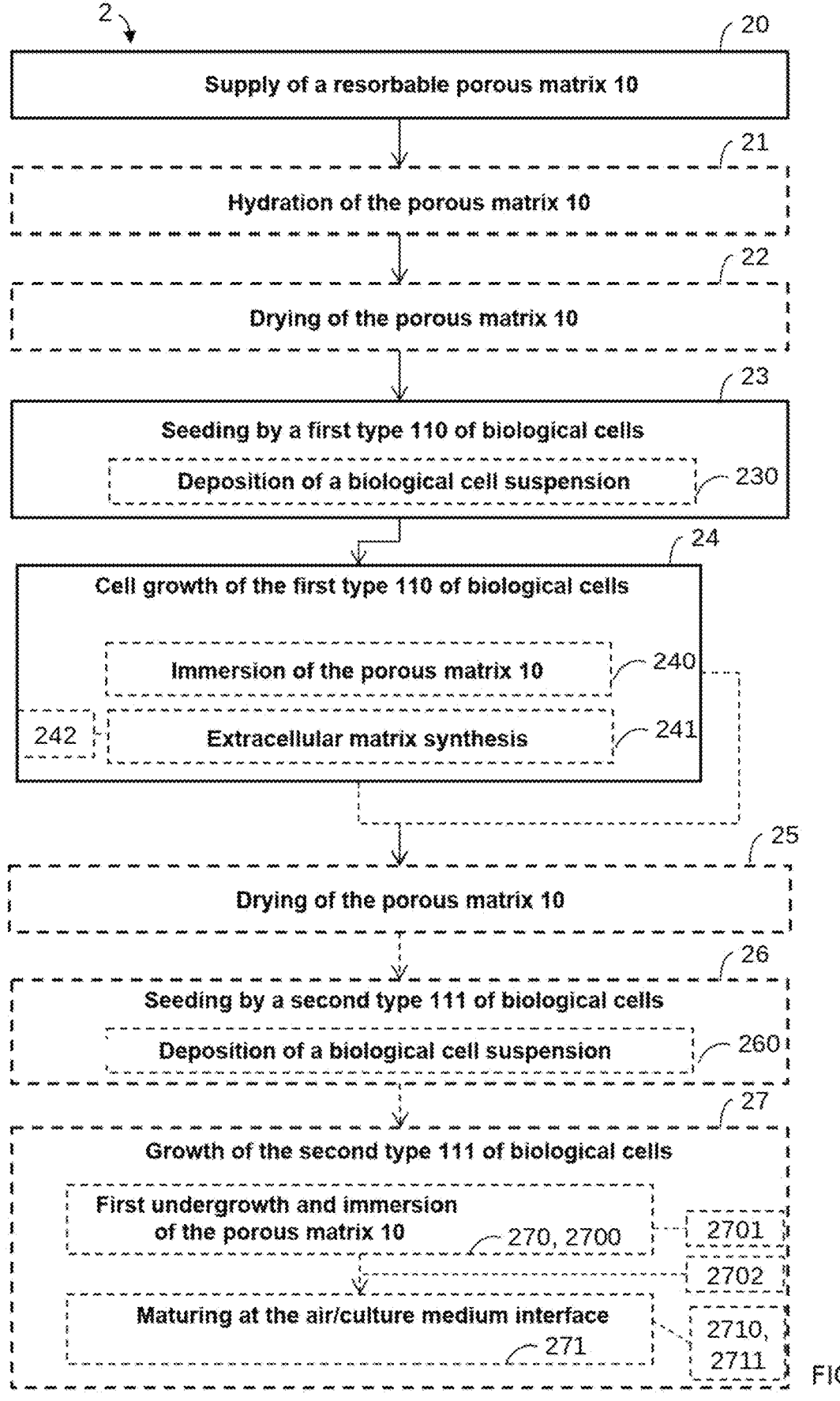
FIG. 6 represents the steps of the method for manufacturing the biomaterial, according to an embodiment of the invention.

The method 2 for manufacturing the biomaterial 1 is now described with reference to FIGS. 1 to 6. As an example, the method is illustrated by FIG. 6, where optional steps are indicated as a dotted line.

The method 2 comprises the supply 20 of a porous matrix 20. The porous matrix 20 exhibits pores delimiting an inner volume 100, as for example illustrated in FIG. 1. Equally, the inner volume 100 represents the volume of vacuum or gas inside the matrix 20, and therefore the porosity of the matrix. The porous matrix 20 exhibits an outer surface 101, comprising an upper face 1010, and a lower face 1012. The outer surface 100 of the porous matrix 10 can further comprise at least one side face 1011, even a plurality of side faces 1011, as for example illustrated in FIG. 1.

According to an example, the porosity of the porous matrix 10 is homogenous, i.e. that the porosity by unit of volume is substantially identical in any portion of one same size determined from the porous matrix 10. Thus, it is excluded that the inner volume conserved in the porous matrix in the form of a cavity. The dimension of the pores of the porous matrix 10 is preferably greater than the dimension of biological cells 11, and in particular eucaryote biological cells. Thus, the pores of the porous matrix 10 enable the migration of biological cells 11 in the inner volume 100. Additional features of the porous matrix 10 are described below.

The porous matrix 10 can be prepared in view of a seeding 23 of biological cells 11. For this, the method 2 can comprise a hydration 21 configured to balance the pH and the osmolarity of the porous matrix around values corresponding to the native environment of the cells. This makes it possible to obtain a homogenous osmolarity in the porous matrix 10, and thus a better migration and colonisation of the seeded cells 11. This is particularly advantageous when the porous matrix 10 is thick, for example, when the porous matrix 10 is a sponge. As an example, to manufacture a dermoepidermal substitute, this pH can be between 6.8 to 7.5, and the osmolarity can be between 270 and 360 mmol/kg. For comparison, in vivo the cell osmolarity is substantially equal to 290 mmol/kg and the cell pH is substantially equal to 7.4. During hydration 21, the porous matrix 10 can be immersed in a buffered solution for several hours, even several days. The porous matrix 10 can further be immersed in a culture medium 3 configured to correspond to the native environment of the cells. As an example, to manufacture a dermoepidermal substitute, the culture medium 3 can be a medium equal to the medium of the dermis.

Following its hydration 21, the method 2 can comprise a drying 22 of the porous matrix 2 to favour the adhesion of biological cells 11 on the porous matrix during their seeding 23, and therefore their subsequent cell growth 24. For example, the drying of the porous matrix 10 can be performed by aspiration of the hydration solution.

The method 2 then comprises a first seeding 23 of the porous matrix by living biological cells 11 of a tissue, and more specifically, by at least one first type 110 of biological cells 11. Thus, biological cells 11 are added to the porous matrix 10 to form a biomaterial 11 being close to a native tissue, relative to a biomaterial formed only from an inert material.

The biological cells 11 can be eucaryote, human or animal cells. Below, a non-limiting example is referred to, where the biological cells 11 are human cells.

The biological cells 11 can be chosen from among cells derived from standard cell line cultures and cells isolated from a biological sample of an organism. A biomaterial 1 comprising cells 11 derived from standard cell line cultures makes it possible to form an efficient tissue substitute, while remaining at a reduced cost, which is particularly advantageous for pharmaceutical or cosmetic applications. The standard cell line cells can be available on the market at vendors known to a person skilled in the art.

According to an example, the biological cells can be autologous or allogenic. The allogenic biological cells can, for example, be isolated from operatory residue, in particular, independently from a skin graft. A biomaterial 1 comprising autologous cells 11 makes it possible to be personalised for a given person, which is particularly advantageous for medical applications, like for example, a graft of the biomaterial 1. In the case of autologous cells, the biological cells can be isolated from a biological sample of a person, for example, following one or more biopsies, and in particular a skin biopsy.

The biological cells 11 can comprise cells chosen from among conjunctive tissue cells and epithelial cells. As an example, the dermis, the subcutaneous fat tissue, the corneal stroma, the bones can be cited as a conjunctive tissue, and as an epithelial tissue, the epidermis and the epithelium of the cornea. According to an example, the conjunctive tissue cells are dermis cells called fibroblasts. According to an example, the epithelial cells are cells of the epidermis called keratinocytes. Thus, and as described in more detail below, the biomaterial 1 can form a skin substitute, even dermoepidermal substitute, for in vitro or in vivo applications.

Below, the non-limiting example is referred to, wherein a first type of cell comprises, even is constituted, of dermis cells, and more specifically, fibroblasts, and a second type of cell comprises, even is constituted, of epidermis cells, and more specifically, keratinocytes. It is noted that for the manufacturing of a skin substitute, even dermoepidermal substitute, it can be provided that the first type of biological cells comprises, in addition to the cells of the dermis, at least one type of biological cells from among:

endothelial cells, to obtain a vascularised dermis,
  immune cells, to obtain an immunocompetent dermis,
  stem cells of the fat tissue, to obtain a subcutaneous fat structure.

According to an example, the second type of biological cells can further comprise melanocytes, to obtain a pigmented epidermis. The biomaterial is thus complexified and is closer to native skin, in particular in terms of diversity of biological cells present in the tissue, and physiological functions.

Figure 2:
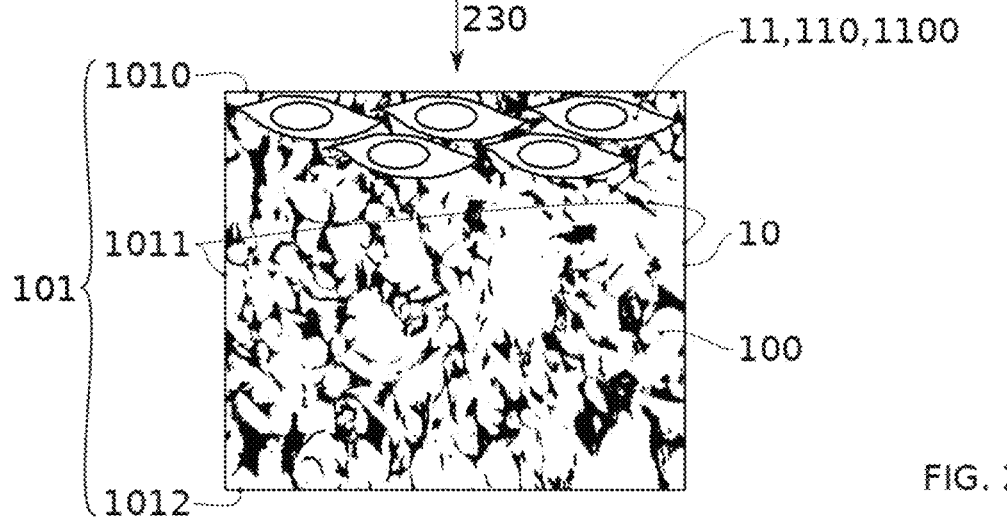
FIG. 2 represents a first seeding of the porous matrix illustrated in FIG. 1 by a first type of biological cells, according to an embodiment of the invention.

The fibroblasts 1100 can be seeded 23 by the deposition 230 of a cell suspension, for example, drop-by-drop on the surface 101 of the porous matrix, and in particular on its upper face 1010 according to the example illustrated in FIG. 2. According to an example, the fibroblasts 1100 can be seeded at a cell density of between 500000 and 1000000 cells/cm$^2$, even substantially 800000 cells/cm$^2$. It is noted that according to the type of seeded biological cells, the cell density can be adapted. Thus, the fibroblasts 1100 can penetrate into the inner volume 100 of the porous matrix 10. To further facilitate the adhesion of the seeded 23 fibroblasts 1100, the method can further comprise a step of adhering the cells 11, during which the porous matrix 10 is left to the open air for a determined time, for example several minutes, even one hour, even preferably in an atmosphere containing 5% of $CO_2$.

Figure 3:
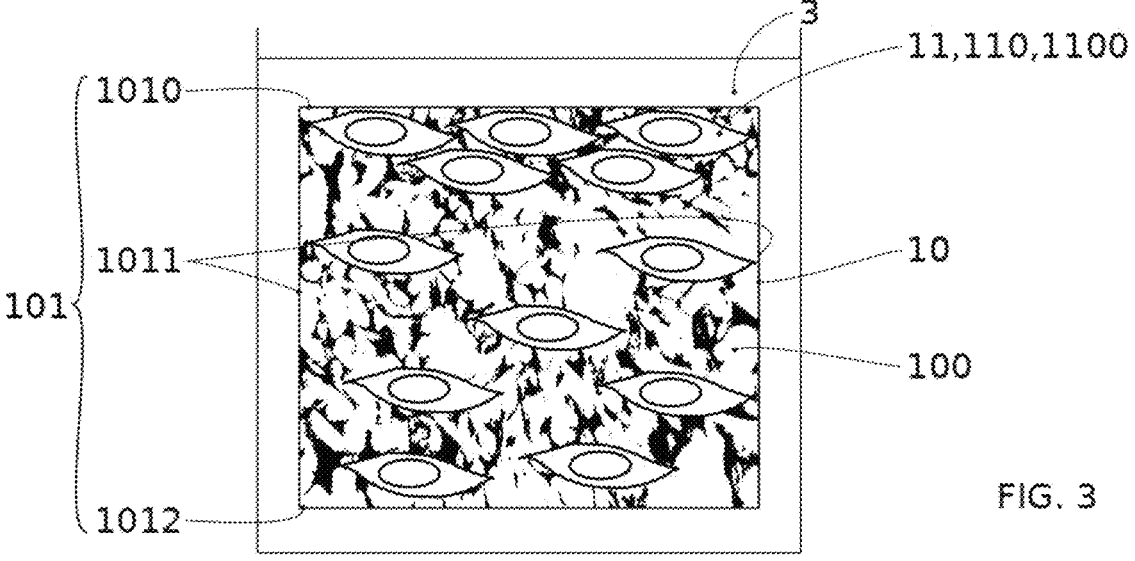
FIG. 3 represents the cell growth of the biological cells following the seeding illustrated in FIG. 2, according to an embodiment of the invention.

The method 2 then comprises a cell growth 24 of the seeded 23 fibroblasts 1100. The fibroblasts 1100 can multiply by cell division at least in the inner volume 100 of the porous matrix 10 to colonise at least partially, the inner volume 100, even all of it, as illustrated by FIG. 3. During the cell growth 24, the fibroblasts can further synthesise 241, or equally secrete, an extracellular matrix 112 at least in the inner volume 100. The biological cells 11, and in particular, the fibroblasts 1100, and their extracellular matrix 112 make it possible to form a tissue in the porous matrix 10, and be closer to the properties of a native tissue, and in particular a native skin. The fibroblasts 1100 in the inner volume 100 of the porous matrix 10, even the fibroblasts 1100 and their extracellular matrix 112, thus form a skin substitute equal to the native dermis.

To enable the cell growth 24 of the fibroblasts 1100, the porous matrix 10 with the seeded 23 fibroblasts 1100 can be immersed at least partially, and preferably, totally, in a culture medium 3 configured to mimic the native environment of the fibroblasts 1100, as illustrated in FIG. 3. With the matrix 10 being porous, the culture medium 3 is thus distributed homogenously in the porous matrix 10 to facilitate cell growth 24. For example, the culture medium is a medium equal to the medium of the dermis, i.e. the properties of which, even the composition, is substantially equal to the medium of the dermis. During cell growth 24, the culture medium 3 can further be renewed 242, typically at a frequency of several times a week. Following a first immersion in a culture medium 3 having no ascorbic acid and no epidermal growth factor (EGF), the subsequent medium renewals 24, can be performed with a culture medium 3 comprising the ascorbic acid of the EGF. According to an example, the first renewal 242 of mediums occurs 24 to 48 hours after the seeding 23 of the fibroblasts 1100.

It is noted that according to the type, other cell types which can be seeded with the fibroblasts 1100, the medium can be configured to be adapted to mimic the environment more favourable to the seeded cell types.

The method 2 can further comprise a second seeding 26, for example performed after one or more weeks of cell growth 24 of the fibroblasts 1100. Prior to the second seeding 26, the porous matrix 10 can be dried 25 similarly to the drying 22 described above. Then, a second type 111 of biological cells 11 can be seeded 26, comprising, in particular, keratinocytes 1110.

The dryings 22, 25 prior to the seedings make it possible to favour the cell adhesion of the cells 11 seeded on the porous matrix, and therefore their subsequent cell growth, as indicated above for the drying 22. Furthermore, the culture medium can be renewed or changed. The drying of the porous matrix 10 can comprise an aspiration of the solution or of the cell medium present in the porous matrix 10. According to an example, during the drying, the porous matrix 10 can further be deposited on an absorbent support. The porous matrix 10 can, for example, be deposited on a sterile compress, preferably deposited on a sterile blotting paper. Preferably, the porous matrix 10 is deposited on the absorbent support after aspiration. The aspiration makes it possible to remove the solution or the medium present in the porous matrix 10 in a controlled and precise manner. The deposition on the absorbent support makes it possible to finalise the drying of the porous matrix 10 and thus further improve the cell adhesion of the cells 11 seeded on the porous matrix 10.

Figure 4:
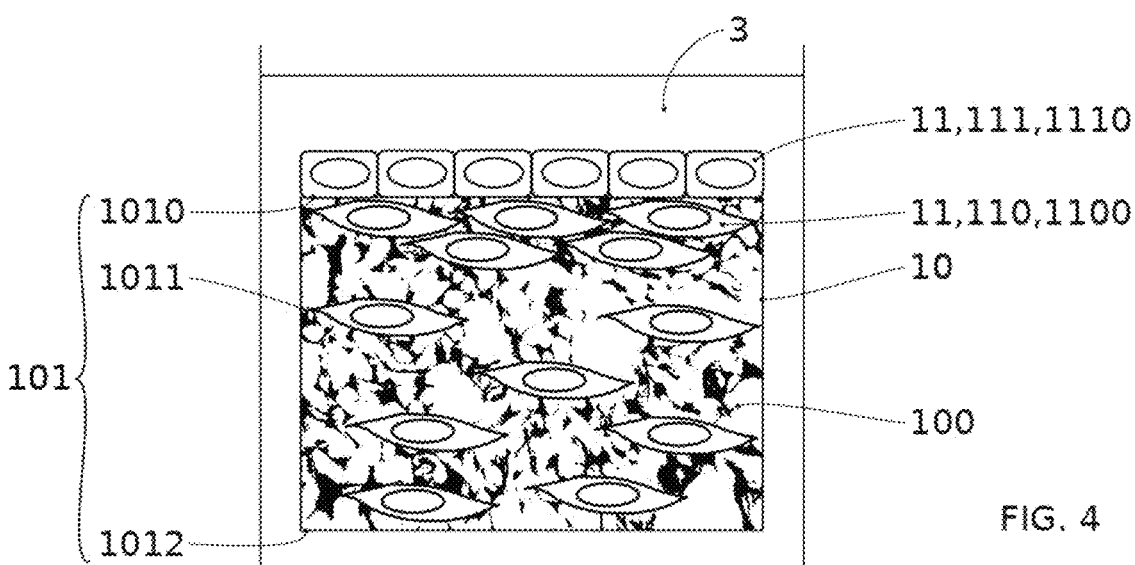
FIG. 4 represents a second seeding of the porous matrix by a second type of biological cells and a first subsequent cell undergrowth of the second type of biological cells, following the cell growth illustrated in FIG. 3, according to an embodiment of the invention.

The keratinocytes 1110 can be seeded 26 by the deposition 260 of a cell suspension, for example, drop-by-drop on the surface 101 of the porous matrix 10, and in particular on its upper face 1010 according to the example illustrated in FIG. 4. Preferably, the deposition of the cell suspension on the side faces 1011 of the porous matrix 10 is avoided, to avoid the propagation of keratinocytes 1110 on these faces. The keratinocytes 1110 can be seeded at a cell density of between 500000 and 1000000 cells/cm$^2$, even substantially 800000 cells/cm$^2$. It is again noted that according to the type of seeded biological cells, the cell density can be adapted. The seeded 26 keratinocytes 1110 remain on the outer surface 101 of the porous matrix 10 by the presence of the extracellular matrix secreted by the fibroblasts and by the presence of the fibroblasts themselves. To further facilitate the adhesion of the seeded 26 keratinocytes 1110, the method can further comprise a step of adhering the cells 11, during which the porous matrix 10 is left for a determined time, for example several minutes, even one hour, and preferably in an atmosphere containing 5% $CO_2$ and at 37° C.

The method 2 then comprises a cell growth 27 of the seeded 26 keratinocytes 1110. Thus, the keratinocytes 1110 multiply by cell division on the outer surface 101 of the porous matrix 10 until the confluence 2702 of the keratinocytes 1110, as illustrated by FIG. 4.

The keratinocytes 1110 on the surface 101 of the porous matrix 10, thus form an epidermal substitute, equal to the native epidermis. It is understood that with the fibroblasts 1100, even with their extracellular matrix 112, the biomaterial 1 can form a dermoepidermal substitute equal to native skin.

For this, the cell growth 27 of the keratinocytes 1110 can comprise a first undergrowth 270 during which the porous matrix 10 with the seeded cells 23, 26 is immersed in a culture medium 3 configured to mimic the native environment of the keratinocytes 1110, for example a medium called MC2, adapted from the "Green" medium such as described below. The addition of the culture medium 3 is preferably performed without the incident medium flow 3 does not directly touch the surface 101 of the porous matrix 10, so as to not disrupt the adhered keratinocytes 1110, and until covering the porous matrix and the cells, including the keratinocytes 1110. The matrix 10 being porous, the culture medium 3 is thus distributed homogenously in the porous matrix 10 to facilitate the cell growth 27. Furthermore, during cell growth 26, the culture medium 3 can further be renewed 2701, typically at a frequency of several times a week.

Following a first immersion in a culture medium 3 having no ascorbic acid and EGF, the subsequent renewals 2701 of medium occur 24 to 48 hours after the seeding 26 of the keratinocytes 1110.

Following the first undergrowth, the cell growth 27 of the keratinocytes 1110 can comprise a maturing 271 during which the porous matrix 10 is placed at an interface 5 between the air 4 and a culture medium 3. This configuration makes it possible to induce a differentiation 2710 of the keratinocytes 1110' to form a complex, even complete epidermis, characterised by a pluristratification and a differentiation as illustrated in FIG. 5A. Furthermore, during and following the maturing, it is possible to observe the expression of specific proteins or lipids linked to the differentiation of keratinocytes 1110, such as cytokeratin 1 or 10, loricrin, involucrin or filaggrin, or at their proliferative state, such as cytokeratin 5 or 14, ki67. The biomaterial 1 is closer to a native skin, in particular in terms of diversity of biological cells present in the tissue, and of physiological functions. More specifically, the keratinocytes 1110' can be differentiated to form at least some, even all of the following layers of the epidermis, given from inside to outside:

stratum germinativum: composed of one single keratinocyte site at the junction with the dermis, these cells being capable of proliferating, stratum *spinosum*: composed of 5 to 6 polygonal keratinocyte sites, stratum *granulosum*: composed of 2 to 4 flat and fusiform keratinocyte layers, stratum corneum.

According to the example illustrated in FIG. 5A, the porous matrix 10 with the seeded cells 23, 26 can be disposed on an absorbent support 7, placed on a grid 6, for example made of stainless steel metal and sterilisable by autoclave. An adapted culture medium 3, called air/liquid medium, can then be added to as to be flush with the absorbent support 7, for example a blotting paper. Thus, the porous matrix is kept hydrated, while enabling the induction of the differentiation of the keratinocytes 1110. Preferably, the level of the culture medium 3 is adjusted so as to avoid the presence of bubbles under the grid 6, even between the absorbent support 7 and the grid 6. Furthermore, during the maturing 271, the air/liquid culture medium, preferably only added with vitamin C, can further be renewed 2711, typically at a frequency of several times a week.

Figure 7:
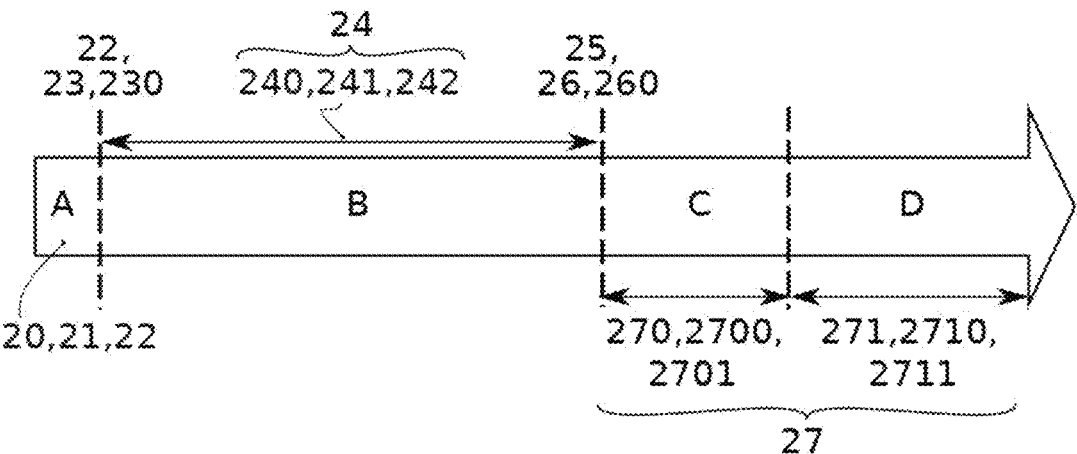
FIG. 7 represents a chronology of the steps of the method for manufacturing the biomaterial, according to an embodiment of the invention.

As an example, a chorology of steps of the manufacturing method 2 is given with reference to FIG. 7. In a first phase A, the porous matrix 10 can be supplied 20, then prepared by hydration 21 and drying 22. The fibroblasts 1100 can then be seeded 23 on a designated day J0. In a second phase B, the cell growth 24 of the fibroblasts can be performed, following which the keratinocytes 1110 can be seeded 26, 14 to 21 days after J0. In a third phase C, the first undergrowth 270 of the keratinocytes 1110 can be performed, 21 to 28 days after J0, the porous matrix 10 can be disposed at the interface 5 between the air and the culture medium 5 to enable the cell differentiation 2710 in a phase D, for example during 7 to 21 days. It is noted that the durations indicated can vary as needed and the available quantity of cells.

By the features of the method 2 described, it is understood that the biomaterial 1 can be obtained according to the first aspect of the invention, comprising, in particular, at least one type 110 of living biological cells 11 of a tissue, disposed in the inner volume 100. Alternatively or complementarily, the type 110 of living biological cells 11 of a tissue can be disposed on the surface 101 of the porous matrix 10. In particular, the arrangement of the cells 11 in the porous matrix 10 can depend on the nature of seeded biological cells 11. In the case of the cornea, stromal cells of the cornea can be deposited in the porous matrix 10 to form the stroma, and keratocytes can be deposited on the surface of the porous matrix 10 to form the epithelium of the cornea. More specifically, the biomaterial 1 can form a dermoepidermal substitute of a native skin, as illustrated in FIG. 5B.

The biomaterial 1 can, in particular, be used for an in vitro application of pharmaceutical substances or cosmetic substances. During the development of the invention, it has been highlighted that the method described makes it possible to obtain the material 1 in a reproducible manner. Moreover, the biomaterial 1 can be used as a model tissue, for example for fundamental and dermatological research.

By the features described above, the biomaterial 1 exhibits a regenerative activity. The biomaterial 1 is thus particularly suitable for the treatment of lesions and/or for a graft, for example on the skin, on the eye or on a bone.

The biomaterial 1 could form a dermoepidermal substitute of a native skin, obtained in a reproducible manner, the biomaterial 1 is particularly suitable for testing new products in the pharmaceutical industry. For example, skins reconstructed from patient cells can represent an alternative model for the modelling of dermatological diseases, such as vitiligo, psoriasis, atopic dermatitis and Xeroderma Pigmentosum, and for the development of therapeutic molecules.

The biomaterial 1 forming a dermoepidermal substitute of a native skin, the biomaterial 1 can in particular be used to:

treat burn sequelae,
treat an acute skin wound,
treat a chronic skin wound,
treat skin donor areas once a tissue sample is performed,
perform a skin graft, for example following a burn, an ulcer, a skin trauma,
treat any loss of skin or dermoepidermal substance.

The biomaterial 1 forming a dermoepidermal substitute of a native skin, is particularly adapted for the treatment of chronic wounds or of a burn as it minimises, even avoids, the addition of a trauma of iatrogenic origin, linked to the skin removal at a donor area. Furthermore, the biological cells 11 could be autologous, the biomaterial 1 minimises the risk of immune rejection of the biomaterial 1.

To obtain the autologous cells 11, a skin biopsy can be performed, on a health surface and reduced relative to the necessary surface for the treatment of a wound or of a burn. The cells 11 can be multiplied by cell proliferation in the manufacturing method 2 in order to obtain a sufficient quantity to enable cell growths 24 and/or 27. It is therefore possible to obtain a biomaterial 1 exhibiting a surface adapted to the surface of the injured area. Thus, the biomaterial 1 and its manufacturing method 2 make it possible to minimise the risks and trauma linked to the skin removal in a person, relative to the current solutions.

Furthermore, the biomaterial 1 can be used as a skin substitute for the in vitro test of pharmaceutical substances, for example of dermatological medications, and of dermo-cosmetic products. The effectiveness and innocuity tests for dermatological medications and dermocosmetic products can thus be performed on a biomaterial being close to a native skin.

Features of the biomaterial 1 have been described during the description of the method 2. Below, additional features of the biomaterial 1 are detailed.

The porous matrix 10 of the biomaterial 1 is now described in detail. The porous matrix 10 can be elastically deformable, for example, under the pressure of a finger of a user. Thus, the use of the biomaterial 1 is facilitated, for example for its application on an injured area. The barrier properties of biomaterial 1 can, for example, be improved.

The porous matrix 20 is resorbable. The porous matrix 20 can further be biocompatible, in particular by being constituted of biocompatible materials. The porous matrix can more specifically be formed of a material comprising collagen. The collagen can be type I bovine or porcine collagen. The material of the porous matrix 10 can comprise at least 90%, preferably at least 95%, and more preferably at least 99% by mass of collagen, relative to the dry mass of the porous matrix 10. Thus, the integration in the organism of a part of the biomaterial 1, and more specifically, of the tissue formed by the biological cells 11 is facilitated.

Furthermore, the material of the porous matrix 10 can have no chitosan. Chitosan exhibits a degradation speed in an organism less than that of collagen. As the biomaterial 1 comprises biological cells 11, it is not necessary to wait for the cells of a person to colonise the biomaterial following their implant, for example by graft, as for the current solutions. Subsequently, it is possible to use a porous matrix with the basis of a material exhibiting a quicker degradation speed. It can even be advantageous to accelerate the degradation of the porous matrix to accelerate the integration of the tissue formed by the biological cells.

The porous matrix 10 can be in the form of a gel, and more specifically, of a powder or of a sponge. Thus, the porous matrix can be shaped two, even three-dimensionally as needed. According to an example, the porous matrix 10 is a synthetic sponge, and more specifically, a haemostatic sponge. A synthetic sponge can easily be shaped by cutting and exhibits a hardness, enabling it to preserve the desired shape, while remaining sufficiently deformable to be able to be applied on a support, for example on the body of a person. A haemostatic sponge is a synthetic sponge, generally composed of materials of biological origin, and resorbable by the organism. The porosity of these sponges enables a great absorption of incoming fluid, typically up to 35 times their weight. A haemostatic sponge is presented as a dry, flexible, porous material, commercially available in various forms and commercial brands. Thus, the porous matrix 10 can be available commercially and at a reduced cost.

A haemostatic sponge makes it possible to absorb blood from the human and animal body, for example from a wound on which the biomaterial is deposited. A haemostatic sponge can absorb a weight in blood substantially greater than or equal to 10 times, preferably substantially greater than or equal to 20 times, and more preferably, substantially greater than or equal to 30 times the weight of the sponge before absorption. The haemostatic sponge thus produces a pressure on the site of the bleed, inducing a platelet aggregation and therefore activating the coagulation pathways of the fibrin to reach a haemostasis. However, it could be expected that the suctioned blood degrades the cells of the biomaterial. Yet, during the development of the invention, it has been observed, surprisingly, that the aspiration of the blood in the biomaterial 1 did not harm the cells 11 seeded in the biomaterial 1, in particular when the biomaterial 1 comprises an extracellular matrix 112 secreted by the cells 11.

The porous matrix 10 supplied 20 is preferably sterile, in order to avoid the proliferation of undesired organisms in the biomaterial 1. According to an example, the porous matrix 10 is a product according to Good Manufacturing Practices (GMP). Good manufacturing practices are regulatory texts established by the States, the European Commission or the Global Health Organisation, and apply in particular to the manufacturing of medications for human or veterinary use. Equally, the porous matrix 10 is usable clinically on an animal or a person, for example, for its application on a wound. Thus, the process of bringing the biomaterial to the market is simplified.

For example, the porous matrix 10 is a BPF haemostatic sponge chosen from among haemostatic sponges of the following brands: Spongostan™, CuraSpon®, Gelfoam® and Surgifoam®.

Figure 8:
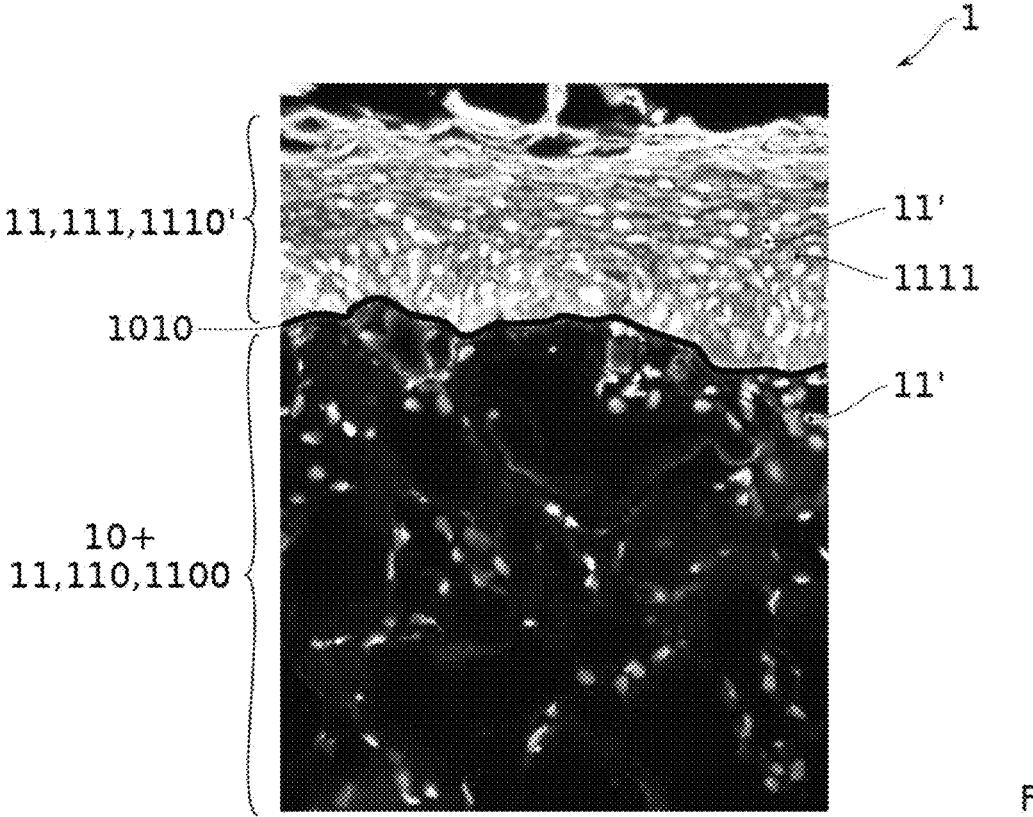
FIG. 8 represents a fluorescent microscopy immunohistologic image as a transverse cross-section of the biomaterial, wherein the nuclei of the biological cells and the cytokeratin 14 are marked.
Figure 9:
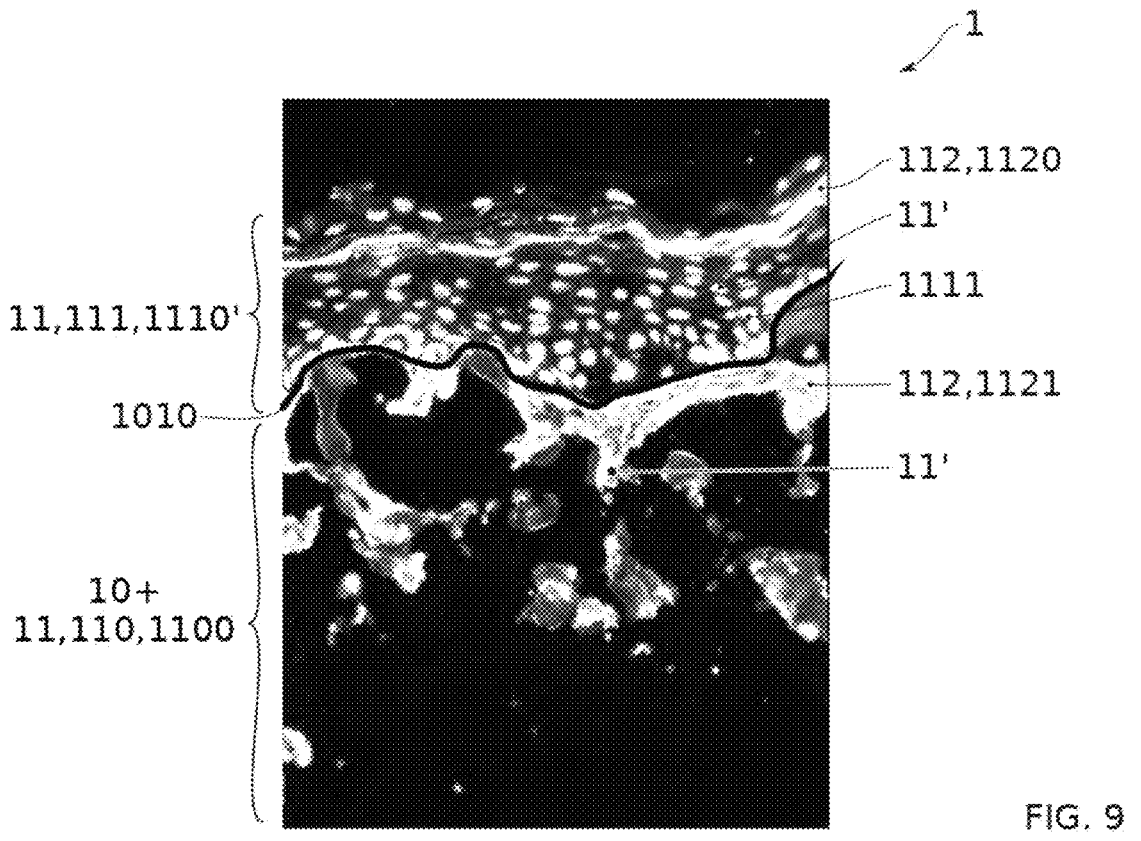
FIG. 9 represents a fluorescent microscopy immunohistologic image as a transverse cross-section of the biomaterial, wherein the nuclei of the biological cells, the filaggrin and the type 1 collagen are marked.
Figure 10:
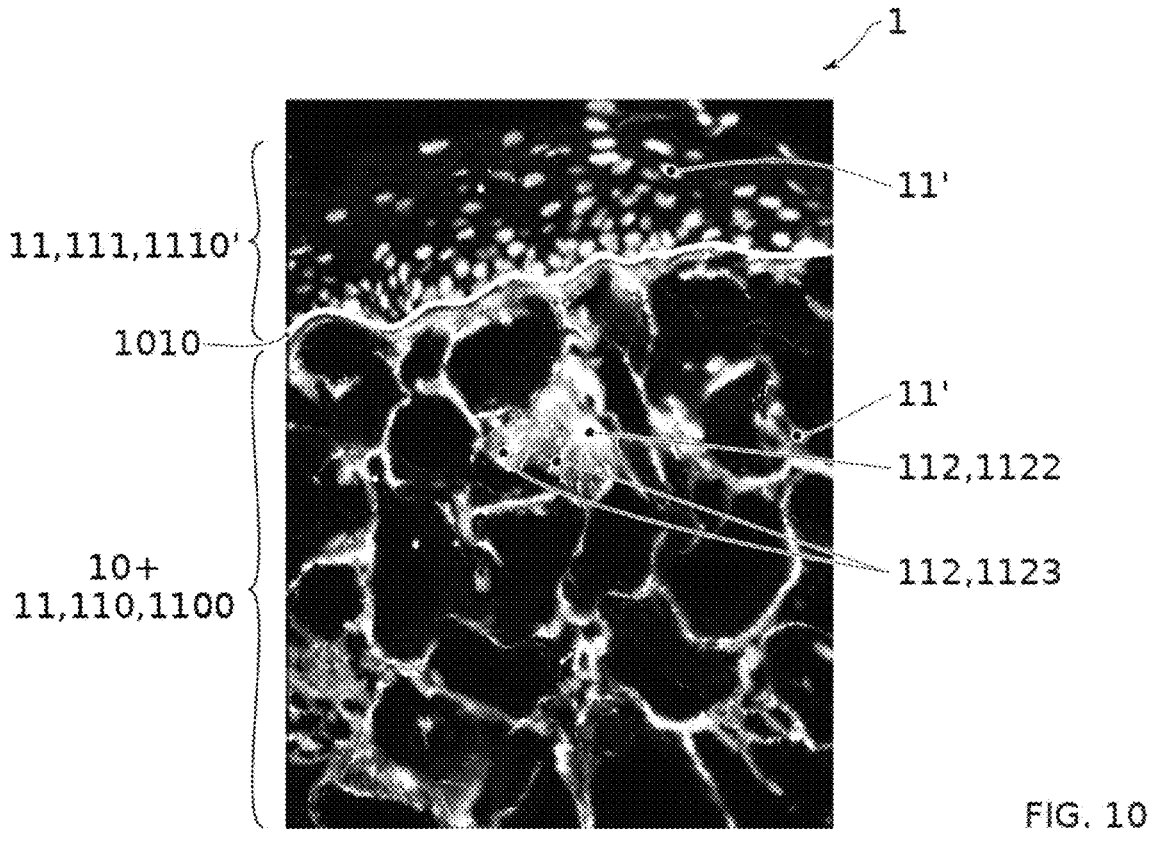
FIG. 10 represents a fluorescent microscopy immunohistologic image as a transverse cross-section of the biomaterial, wherein the nuclei of the biological cells, the fibrillin 1 and the elastin are marked.

As an example, fluorescent microscopy immunohistologic characterisations of the biomaterial 1 according to an embodiment are illustrated by FIGS. 8 to 10. For these characterisations, antibodies specific to certain cell structures, and coupled with a fluorescent probe are applied on the biomaterial 1.

FIG. 8 represents a transverse cross-sectional fluorescent microscopy image of the biomaterial, wherein the nuclei 11' of the biological cells 11 and the cytokeratin 14 1111 are marked. The arrangement of fibroblasts can be observed in the porous matrix 10 and those of the keratinocytes above the upper face 1010 of the porous matrix 10. The differentiated keratinocytes 1110' further exhibit a cytokeratin cytoskeleton 1111.

FIG. 9 represents a transverse cross-sectional fluorescence microscopy image of the biomaterial 1, wherein the nuclei 11' of the biological cells 11, filaggrin 1120 and type I collagen 1121 are marked. The secreted extracellular matrix 112 can be observed, by the marking of the stated proteins, respectively below and above the upper face 1010 of the porous matrix 10.

FIG. 10 represents a transverse cross-sectional fluorescence microscopy image of the biomaterial 1, wherein the nuclei 11 of the biological cells, the fibrillin 1 1122 and the elastin 1123 are marked. The extracellular matrix 112 secreted by the fibroblasts 1100 in the porous matrix 10 can be observed, by the marking of the stated proteins.

Example of an Operating Mode of the Method for Manufacturing the Biomaterial As an example, an operating mode of the method 2 for manufacturing the biomaterial 1 is now described according to a particular embodiment.

The composition of the culture mediums 3 used is given in the following tables. The "qsp" means sufficient quantity of the volume of desired solution. The percentages are given in volume relative to the desired solution volume.
Culture Medium MC1

TABLE 1

| Components | Concentrations |
| --- | --- |
| DMEM/glutamax medium | qsp |
| Bovine serum | 5% |
| Foetal bovine serum | 5% |
| EGF | 10 ng/mL |
| Penicillin | 100 unit/mL |
| Streptomycin | 100 µg/mL |
| Amphotericin B | 1 µg/mL |
| Vitamin C | 82.2 µg/mL |

Culture Medium MC2 Adapted from the GREEN Medium

TABLE 2

| Components | Concentrations | Alternatives for the clinic |
| --- | --- | --- |
| DMEM/glutamax medium | qsp | |
| HAM F12 | qsp | |
| Foetal bovine serum | 10% | |
| Hydrocortisone | 0.4 µg/mL | |
| Insulin | 5 µg/mL | Umuline ® at 0.12 UI/ml |
| Choleratoxin | $10^{-10}$ mol/L | Isuprel ® at 0.4 µg/ml |
| Adenine | 24.3 µg/mL | |
| Triiodothyronine | 2 nM | |
| EGF | 10 ng/ml | |
| Amphotericin B | 100 unit/mL | |
| Penicillin | 100 µg/mL | |
| Streptomycin | 1 µg/mL | |
| Vitamin C | 82.2 µg/mL | |

It is noted that in view of a clinical use, the medium MC2 can be adapted by a person skilled in the art to be compatible with a clinical use.
Culture Medium A/L

TABLE 3

| Components | Concentrations |
| --- | --- |
| DMEM/glutamax medium | qsp |
| HAM F12 | qsp |
| Bovine serum albumin (BSA) | 8 mg/mL |
| Hydrocortisone | 0.4 µg/mL |
| Insulin | 5 µg/mL |
| Amphotericin B | 1 µg/mL |
| Penicillin | 100 unit/mL |
| Streptomycin | 100 µg/mL |
| Vitamin C | 82.2 µg/mL |

The preparation of reagents to manufacture the culture mediums is now described:
preparation of trio-iodo-L-thyronine (abbreviated T3 below):
prepare a solution A at $2\times10^{-4}$M by weighing 13.6 mg of T3, then dissolving it in 1.5 ml of a sodium hydroxide solution NaOH at 0.02 mol/L, completing at 100 mL with sterile water,
prepare the parent solution of $2\times10^{-6}$M by diluting to $1/100^{th}$ of the solution A,
filter a 0.22 µm dimension filter,
aliquot into portion of 550 µL and freezing at −20° C.,
use 500 µL of the solution at $2\times10^{-6}$M for 500 mL of medium MC2 to obtain a final concentration $2\times10^{-9}$M, preparation of adenine:

dissolve 0.486 g of adenine in 3 mL of a NaOH solution at 0.4 mol/L. Add 10 mL of sterile water, then 10 mL of a hydrochloric acid HCl solution at mol/L. Mix and complete with sterile water up to 200 mL, filter a filter of porosity 0.22 μm, aliquot into portion of 5 mL and freeze at −20° C., use 5 mL for 500 mL of medium to obtain a final concentration at 24.3 μg/mL, preparation of EGF:

prepare a solution at 10 μg/mL by returning 200 μg of EGF lyophilised by sterile water into qsp 20 mL, filter on a filter of porosity 0.22 μm, aliquot into portions of 500 μL and freeze at −20° C., use 500 μL for 500 mL of medium at the time of using the culture medium, to obtain a final concentration of 10 ng/mL, Preparation of vitamin C:

weigh 2.5 g of vitamin C in powder and dissolve it progressively in 60.8 mL of DMEM medium at 37° C. to obtain a concentration of 41.1 mg/mL or equally, 142 mmol/L, filter on a filter of porosity 0.22 μm, aliquot into portions of 0.5 ml and freeze at −20° C., use 200 μL in 100 mL of medium to obtain a final concentration of 82.2 μg/mL, preparation of BSA:

weight 4 g of BSA and dissolve it in 20 mL of DMEM medium at 37° C., filter on a filter of porosity 0.22 μm, use 20 mL for 500 mL of medium, preparation of hydrocortisone:

prepare a solution B at 5 mg/mL by dissolving 25 mg in 5 mL of ethanol at 95%, prepare a solution C at 200 μg/mL by taking 0.4 mL of the solution B in 9.6 mL (qsp 10 mL), aliquot the solution C into portion of 1 mL, use 1 mL for 500 mL of medium, to obtain a final concentration of 0.4 μg/mL, preparation of insulin:

re-suspend 50 mg of insulin with 500 μL of an HCL solution at 0.1 mol/L, dilute the suspension obtained in the sterile water qsp 10 mL, to obtain a concentration of 5 mg/mL, filter a filter of porosity 0.22 μm, aliquot into portions of 500 μL, use 500 μL for 500 mL of medium, to obtain a final concentration of 5 μg/mL, preparation of choleratoxin:

re-suspend 1 mg of choleratoxin in 12 mL of sterile water to obtain a concentration of 10.10-7 mol/L, use 500 μL of the solution at $10.10^{-7}$ for 500 mL of medium to obtain a final concentration of $10^{-16}$ mol/L.

The steps of the operating mode are now detailed.

For the extraction of fibroblasts and keratinocytes of a skin biopsy of a patient, the skin biopsy is incubated for 3 hours at 37° C. in a sterile dispase solution. The dermis and the epidermis are thus separated using sterile tweezers then rinsed in sterile PBS 1X.

For the extraction of fibroblasts, the pieces of dermis obtained are then put in a sterile collagenase A solution at 0.5 mg/mL, while stirring, for 4 to 6 hours at 37° C. Then the solution is filtered on a screen of porosity 70 μm and centrifuged at 1200 rotations per minute (abbreviated rpm below) for 5 to 10 minutes. After re-suspension of the pellet, the numeration and the cell viability is evaluated. The fibroblasts are seeded at a density of 8000 cells/cm$^2$.

For the extraction of keratinocytes, the pieces of epidermis are incubated in trypsin-EDTA 0.25% at 37° C. for 15 minutes. After addition of trypsin inhibiting solution, the keratinocyte suspension is then filtered on a screen of porosity 70 μm, centrifuged at 1200 rpm for 5 to 10 minutes and the cell pellet thus obtained is re-suspended in the culture medium to evaluate the numeration and the viability. The keratinocytes are seeded at the density of 8000 cells/cm$^2$.

The fibroblasts and the keratinocytes are cultivated at 37° C. in a humid atmosphere with 5% of $CO_2$, the mediums are renewed 3 times a week and the cells are passed to sub-confluence by the trypsin-EDTA action.

For the preparation of the porous matrix, the porous matrix is hydrated for 6 to 48 hours prior to the seeding of the cells by a PBS 1X bath, the volume of which is sufficient to cover the upper face of the matrix. The PBS can then be suctioned. A volume of medium MC1, without antibiotics, nor EGF, nor vitamin C, the volume being sufficient to immerse by covering the upper face of the matrix, is added in order to balance the pH and the osmolarity of the matrices. Alternatively to this preferable method of preparation, it can be provided to hydrate the porous matrix by a bath of 2 to 3 hours in PBS 1X.

For the seeding of fibroblasts, the fibroblasts are removed and disconnected by enzyme action and counted. A cell suspension for obtaining a cell density of $0.5.10^6$ cells/cells/cm$^2$ is prepared. After having suctioned the culture medium to dry the porous matrix, the fibroblast suspension is deposited drop-by-drop homogenously on the upper face of the porous matrix. The fibroblasts left to adhere for 1 hour in the incubator at 37° C. and in an atmosphere at 5% of $CO_2$.

A sufficient volume for covering the upper face of the porous matrix of medium MC1 with antibiotics, but without EGF nor vitamin C is added for the growth of the fibroblasts. The medium is renewed 3 times a week for 2-3 weeks with a medium MC1 with the addition of antibiotics, EGF and vitamin C.

For the seeding of keratinocytes, the keratinocytes are removed by enzyme action and counted. A cell suspension at $0.5.10^6$ cells/cm$^2$) is prepared. After having suctioned the culture medium from the formed skin substitute, the latter can be transferred onto a sterile compress to absorb the maximum humidity.

The keratinocyte cell suspension is deposited drop-by-drop homogenously on the surface of the matrix, being careful that the cell suspension does not overflow over the side faces of the porous matrix. The keratinocytes are left to adhere for 1 hour in the incubator at 37° C. and in an atmosphere at 5% of $CO_2$.

For the first undergrowth, a sufficient volume for covering the upper face of the matrix of medium MC2 with antibiotics, but without EGF nor vitamin C is added onto the matrix very carefully without touching the samples. The culture medium is renewed 3 times a week for 1 week with a medium MC2 with the addition of antibiotics, EGF and vitamin C.

For the maturing, the porous matrix is deposited after aspiration of the culture medium and drying on a sterile compress on a sterile blotting paper, itself placed on a metal grid. The volume of medium A/L supplemented with antibiotics and vitamin C is adjusted such that it is flush with the level of the blotting paper, while avoiding the presence of bubbles trapped under the metal grid. The medium is renewed 3 times a week with the medium A/L containing antibiotics and vitamin C.

In view of the description above, it clearly appears that the invention proposes a biomaterial being closer to a native tissue.

The invention is not limited to the embodiments described above and extends to all the embodiments covered by the claims.

It can, in particular, be provided that the growth durations and/or the composition of the mediums are adapted for other types of biological cells.

REFERENCES

1 Biomaterial
10 Porous matrix
100 Inner volume
101 Surface
1010 Upper face
1011 Side face
1012 Lower face
11 Biological cells
11' Nuclei
110 First type
1100 Fibroblasts
111 Second type
1110 Keratinocyte
1110' Differentiated keratinocyte
1111 Cytokeratin 14
112 Extracellular matrix
1120 Filaggrin
1121 Type I collagen
1122 Fibrillin
1123 Elastin
2 Method
20 Supply of a porous matrix
21 Hydration of the porous matrix
22 Drying of the porous matrix
23 First seeding
230 Deposition of a biological cell suspension
24 First cell growth
240 Immersion of the porous matrix in a culture medium
241 Extracellular matrix synthesis
242 Renewal of the culture medium
25 Drying of the porous matrix
26 Second seeding
260 Deposition of a biological cell suspension
27 Second cell growth
270 First undergrowth
2700 Immersion of the porous matrix in a culture medium
2701 Renewal of the culture medium
2702 Confluence of the biological cells
271 Maturing
2710 Cell differentiation
2711 Renewal of the culture medium
3 Culture medium
4 Air
5 Air/culture medium interface
6 Grid
7 Porous support

The invention claimed is:

1. A method for manufacturing a biomaterial, comprising: a supply of a resorbable porous matrix formed from a material comprising collagen, the resorbable porous matrix being a haemostatic sponge, and exhibiting an inner volume and an outer surface, a hydration of the haemostatic sponge so as to balance pH and osmolarity of the haemostatic sponge, a drying of the haemostatic sponge after the hydration of the haemostatic sponge, after drying the haemostatic sponge, a first seeding of the resorbable porous matrix haemostatic sponge by at least one first type of living biological cells of a tissue, after the first seeding, a cell growth of the at least one type of biological cells, after the first seeding by said at least one first type of biological cells, a drying of the haemostatic sponge, and following said drying, a second seeding of the haemostatic sponge by at least one second type of biological cells, distinct from the at least one first type of biological cells, after the second seeding, a cell growth of the at least one second type of biological cells, a hydration of the resorbable porous matrix so as to balance pH and osmolarity of the resorbable porous matrix, prior to the seeding, and a drying of the resorbable porous matrix between the hydration of the resorbable porous matrix and the seeding of the resorbable porous matrix to form a biomaterial, the biomaterial comprising: the resorbable porous matrix haemostatic sponge, and the at least one first and the at least one second types of living biological cells of a tissue disposed in the inner volume and alternatively or complementarily on the outer surface of the resorbable porous matrix haemostatic sponge, and wherein the hydration and the subsequent dryings prior to the first and second seedings condition the haemostatic sponge to promote cell adhesion and subsequent cell growth.

2. A biomaterial manufactured according to claim 1, comprising:
a resorbable porous matrix formed from a material comprising collagen having a balanced pH and osmolarity, and exhibiting an inner volume and an outer surface, and
at least one first type and at least one second type of living biological cells of a tissue, the at least one second type of biological cells being distinct from the first type of biological cells disposed in the inner volume and alternatively or complementarily on the surface of the resorbable porous matrix,
wherein the resorbable porous matrix is a haemostatic sponge prepared by hydration to balance the pH and the osmolarity followed by drying prior to the disposition of the at least one first type of living biological cells, and
the at least one first type of living biological cells being seeded in the haemostatic sponge in a first seeding, the at least one second type of living biological cells being seeded in the haemostatic sponge in a second seeding, the haemostatic sponge is prepared by drying the haemostatic sponge after the first seeding and prior to the second seeding.

3. The biomaterial according to claim 2, wherein the material of the resorbable porous matrix comprises at least 90% by mass of collagen, relative to the dry mass of the resorbable porous matrix.

4. The biomaterial according to claim 2, wherein the material of the resorbable porous matrix has no chitosan.

5. The biomaterial according to claim 2, wherein the biological cells comprise cells chosen from among conjunctive tissue cells and epithelial cells.

6. The biomaterial according to claim 2, wherein the at least one type of biological cells is disposed at least in the inner volume of the resorbable porous matrix, the biomaterial further comprising an extracellular matrix in said inner volume, the extracellular matrix being secreted by the at least one first type of biological cells.

7. The biomaterial according to claim 2, wherein the at least one first type of biological cells is disposed in the inner volume of the resorbable porous matrix, and the at least one second type of biological cells is disposed on the surface of the resorbable porous matrix.

8. The biomaterial according to claim 7, wherein the first type of biological cells comprises fibroblasts, and the second type of biological cells comprises keratinocytes.

9. The biomaterial according to claim 2, wherein the biological cells are chosen from among cells derived from standard cell line cultures and cells isolated from a biological sample of an organism.

10. The method according to claim 1, wherein the seeding of the resorbable porous matrix is performed by deposition of a suspension of at least one type of biological cells on the resorbable porous matrix.

11. The method according to claim 1 wherein the second seeding is performed by deposition of a suspension of at least one second type of biological cells on the resorbable porous matrix.

12. The method according to claim 1, wherein the biological cells comprise cells chosen from among conjunctive tissue cells and epithelial cells.

13. The method according to claim 12, wherein, when the biological cells are conjunctive tissue cells, the cell growth comprises an immersion of the resorbable porous matrix in a culture medium.

14. The method according to claim 12, wherein, when the biological cells are epithelial tissue cells, the cell growth comprises a first undergrowth during which the resorbable porous matrix is immersed in a culture medium, until a confluence of the biological cells on the surface of the resorbable porous matrix.

15. The method according to claim 14, wherein the growth comprises, following the first undergrowth, a maturing during which the resorbable porous matrix is placed at an interface between the air and a culture medium.

16. A method for using a biomaterial manufactured by the method according to claim 1, the biomaterial comprising:

a resorbable porous matrix formed from a material comprising collagen, the resorbable porous matrix being a haemostatic sponge, and exhibiting an inner volume and a surface, and at least one first type and at least one second type of living biological cells of a tissue, disposed in the inner volume and/or on the surface of the resorbable porous matrix, the method comprising an in vitro application of at least one substance chosen from among a pharmaceutical substance and a cosmetic substance on the biomaterial.

17. A method for using a biomaterial manufactured by the method according to claim 1, for the treatment of lesions, the method comprising an application of the biomaterial on a lesion, the biomaterial comprising:

a resorbable porous matrix formed from a material comprising collagen, the resorbable porous matrix being a haemostatic sponge, and exhibiting an inner volume and a surface, and at least one first type and at least one second type of living biological cells of a tissue, the at least one second type of biological cells being distinct from the first type of biological cells, disposed in the inner volume and, and/or on the surface of the resorbable porous matrix.

\* \* \* \* \*